(12) United States Patent
Anderson et al.

(10) Patent No.: US 12,303,685 B2
(45) Date of Patent: *May 20, 2025

(54) ELECTRODE CONFIGURATION FOR A MEDICAL DEVICE

(71) Applicant: Medtronic, Inc., Minneapolis, MN (US)

(72) Inventors: Thomas A. Anderson, New Hope, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 237 days.

This patent is subject to a terminal disclaimer.

(21) Appl. No.: 18/062,438

(22) Filed: Dec. 6, 2022

(65) Prior Publication Data

US 2023/0123093 A1   Apr. 20, 2023

Related U.S. Application Data

(63) Continuation of application No. 16/895,133, filed on Jun. 8, 2020, now Pat. No. 11,541,232.

(Continued)

(51) Int. Cl.
*A61N 1/375* (2006.01)
*A61N 1/05* (2006.01)
*A61N 1/362* (2006.01)

(52) U.S. Cl.
CPC ........... *A61N 1/059* (2013.01); *A61N 1/3622* (2013.01); *A61N 1/37512* (2017.08); *A61N 1/37518* (2017.08); *A61N 1/3756* (2013.01)

(58) Field of Classification Search
CPC .. A61N 1/059; A61N 1/37518; A61N 1/3622; A61N 1/37512; A61N 1/3756; A61N 1/0573

See application file for complete search history.

(56) References Cited

U.S. PATENT DOCUMENTS

| 3,814,104 | A | 6/1974 | Irnich et al. |
| 3,943,936 | A | 3/1976 | Rasor et al. |

(Continued)

FOREIGN PATENT DOCUMENTS

| CN | 216022691 U | 3/2022 |
| WO | 2002022202 A2 | 3/2002 |
| WO | 2006118865 A2 | 11/2006 |

OTHER PUBLICATIONS

Haqqani et al., "The Implantable Cardioverter-Defibrillator Lead: Principles, Progress and Promises," PACE, vol. 32, Oct. 2009, pp. 1336-1353.

(Continued)

*Primary Examiner* — Eugene T Wu
(74) *Attorney, Agent, or Firm* — Shumaker & Sieffert, P.A.

(57) ABSTRACT

An example device includes an elongated housing, a first and second electrode, and signal generation circuitry. The housing can be implanted within a single first chamber of the heart. The first electrode extends distally from the distal end of the elongated housing. A distal end of the first electrode can penetrate into wall tissue of a second chamber of the heart. The second electrode, extending from the distal end of the elongated housing, is configured to flexibly maintain contact with the wall tissue of the first chamber without penetration of the wall tissue of the first chamber by the second electrode. Signal generation circuitry can be within the elongated housing and coupled to the first and second electrode. The signal generation circuitry can deliver cardiac pacing to the second chamber via the first electrode and the first chamber via the second electrode.

20 Claims, 13 Drawing Sheets

Related U.S. Application Data

(60) Provisional application No. 62/862,940, filed on Jun. 18, 2019.

(56) References Cited

U.S. PATENT DOCUMENTS

| | | |
|---|---|---|
| 4,103,690 A | 8/1978 | Harris |
| 4,142,530 A | 3/1979 | Wittkampf |
| 4,269,198 A | 5/1981 | Stokes |
| 4,280,512 A | 6/1981 | Karr et al. |
| 4,858,623 A | 8/1989 | Bradshaw et al. |
| 4,936,823 A | 6/1990 | Colvin |
| 5,193,540 A | 3/1993 | Schulman et al. |
| 5,411,535 A | 5/1995 | Fujii et al. |
| 5,573,540 A | 11/1996 | Yoon |
| 5,683,447 A | 11/1997 | Bush et al. |
| 6,007,558 A | 12/1999 | Ravenscroft et al. |
| 6,151,525 A | 11/2000 | Soykan et al. |
| 6,240,322 B1 | 5/2001 | Peterfeso et al. |
| 6,286,512 B1 | 9/2001 | Loeb et al. |
| 6,409,674 B1 | 6/2002 | Brockway et al. |
| 6,575,967 B1 | 6/2003 | Leveen et al. |
| 6,783,499 B2 | 8/2004 | Schwartz |
| 6,915,149 B2 | 7/2005 | Ben-Haim |
| 6,978,178 B2 | 12/2005 | Sommer et al. |
| 7,290,743 B2 | 11/2007 | Nowack |
| 7,418,298 B2 | 8/2008 | Shiroff et al. |
| 8,353,940 B2 | 1/2013 | Benderev |
| 8,798,740 B2 | 8/2014 | Samade et al. |
| 8,948,883 B2 | 2/2015 | Eggen et al. |
| 9,020,611 B2 | 4/2015 | Khairkhahan et al. |
| 9,119,959 B2 | 9/2015 | Rys et al. |
| 9,242,102 B2 | 1/2016 | Khairkhahan et al. |
| 9,526,891 B2 | 12/2016 | Eggen et al. |
| 11,097,114 B2 | 8/2021 | Taff et al. |
| 11,541,232 B2 | 1/2023 | Anderson et al. |
| 2002/0103424 A1 | 1/2002 | Swoyer et al. |
| 2002/0165589 A1 | 11/2002 | Imran et al. |
| 2003/0088301 A1 | 5/2003 | King |
| 2004/0147973 A1 | 7/2004 | Hauser |
| 2004/0230281 A1 | 11/2004 | Heil et al. |
| 2006/0084965 A1 | 4/2006 | Young |
| 2006/0085039 A1 | 4/2006 | Hastings et al. |
| 2006/0085041 A1 | 4/2006 | Hastings et al. |
| 2008/0103539 A1 | 5/2008 | Steggeman et al. |
| 2009/0082828 A1 | 3/2009 | Ostroff |
| 2012/0172892 A1 | 7/2012 | Grubac et al. |
| 2013/0324825 A1 | 12/2013 | Ostroff et al. |
| 2014/0005762 A1 | 1/2014 | Wu et al. |
| 2014/0039591 A1 | 2/2014 | Drasler et al. |
| 2014/0107723 A1 | 4/2014 | Hou et al. |
| 2014/0303704 A1 | 10/2014 | Suwito et al. |
| 2015/0025612 A1* | 1/2015 | Haasl ............... A61N 1/0573 607/127 |
| 2015/0039070 A1 | 2/2015 | Kuhn et al. |
| 2016/0045744 A1 | 2/2016 | Gillberg et al. |
| 2016/0059002 A1 | 3/2016 | Grubac et al. |
| 2016/0296761 A1 | 10/2016 | Doan et al. |
| 2017/0368347 A1 | 12/2017 | Muessig et al. |
| 2018/0280685 A1 | 10/2018 | Toy et al. |
| 2019/0076664 A1 | 3/2019 | Ollivier |
| 2019/0083779 A1 | 3/2019 | Yang et al. |
| 2019/0083800 A1 | 3/2019 | Yang et al. |
| 2020/0054883 A1 | 2/2020 | Eby et al. |
| 2020/0306551 A1 | 10/2020 | Cheng et al. |
| 2022/0047877 A1 | 2/2022 | Mar et al. |
| 2022/0062630 A1 | 3/2022 | Yang et al. |

OTHER PUBLICATIONS

International Search Report and Written Opinion of International Application No. PCT/US2020/038096, mailed Oct. 23, 2020, 11 pp.

Prosecution History from U.S. Appl. No. 16/895,133, dated Sep. 29, 2021 through Sep. 2, 2022, 61 pp.

Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.

Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

* cited by examiner

ELECTRODE CONFIGURATION FOR A MEDICAL DEVICE

This application is a continuation of U.S. patent application Ser. No. 16/895,133, filed Jun. 8, 2020, which claims the benefit of U.S. Provisional Application Ser. No. 62/862,940, filed Jun. 18, 2019, the entire content of each application is incorporated herein by reference.

FIELD

The disclosure relates to medical devices, and more particularly to electrodes of medical devices.

BACKGROUND

Various types of implantable medical devices (IMDs) have been implanted for treating or monitoring one or more conditions of a patient. Such IMDs may be adapted to monitor or treat conditions or functions relating to heart, muscle, nerve, brain, stomach, endocrine organs or other organs and their related functions. Such IMDs may be associated with leads that position electrodes at a desired location, or may be leadless with electrodes integrated with and/or attached to the device housing. These IMDs may have the ability to wirelessly transmit data either to another device implanted in the patient or to another instrument located externally of the patient, or both.

A cardiac pacemaker is an IMD configured to deliver cardiac pacing therapy to restore a more normal heart rhythm. Such IMDs sense the electrical activity of the heart, and deliver cardiac pacing based on the sensed electrical activity, via electrodes. Some cardiac pacemakers are implanted a distance from the heart, and coupled to one or more leads that intravascularly extend into the heart to position electrodes with respect to cardiac tissue. Some cardiac pacemakers are sized to be completely implanted within one of the chambers of the heart, and may include electrodes integrated with or attached to the device housing rather than leads. Some cardiac pacemakers provide dual chamber functionality, by sensing and/or stimulating the activity of both atria and ventricles, or other multi-chamber functionality. A cardiac pacemaker may provide multi-chamber functionality via leads that extend to respective heart chambers, or multiple cardiac pacemakers may provide multi-chamber functionality by being implanted in respective chambers.

SUMMARY

In general, this disclosure is directed to configurations of the electrodes of devices having housings sized for implantation within a single chamber of the heart. More particularly, this disclosure is directed to configurations of electrodes that allow a single device implanted in one chamber to sense in and/or deliver cardiac pacing to more than one chamber. A single device implanted in one chamber that is able to sense in and/or deliver cardiac pacing to more than one chamber may avoid the need for a leaded device or multiple smaller devices to provide such functionality, which may reduce the amount of material implanted within the patient. In some cases, multiple devices may also need to implement energy-intensive communication schemes to coordinate their activities to provide dual chamber functionality.

In some examples, the device includes a first electrode that is configured to penetrate through wall tissue of the heart chamber in which the device is implanted, and into wall tissue of another heart chamber. In addition to the first electrode, the device includes a second electrode configured to maintain consistent contact with the wall tissue of the chamber in which the device is implanted, without penetration of the wall tissue. The electrodes can be connected to a distal end of the device.

The second electrode may be configured to elastically deform, e.g., toward the distal end of the housing of the device, in order to accommodate differences in tissue surface and/or changes in the distance between distal end of the device and the wall tissue during the cardiac cycle. The second electrode may be spring biased toward a resting configuration and, when elastically deformed, the spring bias may urge the second electrode away from the distal end of the device. In this manner, the elastic deformation and spring bias may maintain the second electrode in consistent contact with the wall tissue of the chamber in which the device is implanted.

The capability of the electrode to elastically deform to vary the distance that the electrode extends from the device can, at least in part, help maintain contact between the tissue surface and the electrode, without requiring penetration of the tissue of the first chamber. In this way, the device is not limited to one specific distance for the electrode extending from the device to achieve sufficient contact. Instead, the device may be positioned at varying distances from the tissue surface and the second electrode may with heart motion to maintain contact of the second electrode with the wall tissue. Due to the ability of the second electrode to maintain contact with the wall tissue surface while the other electrode is positioned in wall tissue of another chamber, a single device can provide pacing to two different chambers at the same time.

In one example, a device includes an elongated housing, a first electrode, a second electrode, and signal generation circuitry. The elongated housing extends from a proximal end of the housing to a distal end of the housing, and is configured to be implanted wholly within a first chamber of the heart, the first chamber of the heart having wall tissue. The first electrode extends distally from the distal end of the elongated housing, wherein a distal end of the first electrode is configured to penetrate into wall tissue of a second chamber of the heart that is separate from the first chamber of the heart. The second electrode extends from the distal end of the elongated housing, wherein the second electrode is separate from the first electrode and wherein the second electrode is configured to flexibly maintain contact with the wall tissue of the first chamber without penetration of the wall tissue of the first chamber by the second electrode. The signal generation circuitry is within the elongated housing, coupled to the first electrode and the second electrode, and configured to deliver cardiac pacing to the second chamber via the first electrode and the first chamber via the second electrode.

In another example, a method comprises delivering cardiac pacing from a device to a heart, wherein the device comprises an elongated housing, extending from a proximal end of the housing to a distal end of the housing, and implanted wholly within a first chamber of the heart, the first chamber having wall tissue. The device comprises a first electrode extending distally from the distal end of the elongated housing, wherein a distal end of the first electrode penetrates into wall tissue of a second chamber of the heart that is separate from the first chamber of the heart. The device comprises a second electrode extending from the distal end of the elongated housing, wherein the second electrode is separate from the first electrode and wherein the second electrode is configured to flexibly maintain contact with the wall tissue of the first chamber without penetration of the wall tissue of the first chamber by the second electrode. Delivering the cardiac pacing comprises delivering cardiac pacing to the second chamber via the first electrode, and delivering cardiac pacing to the first chamber via the second electrode.

In another example, a device comprises an elongated housing, a first electrode, a second electrode, and signal generation circuitry. The elongated housing extends from a proximal end of the housing to a distal end of the housing, defines a longitudinal axis, and is configured to be implanted wholly within an atrium of the heart. The first electrode extends distally from the distal end of the elongated housing and comprises a helix, wherein, as the helix is rotated about the longitudinal axis, a distal end of the first electrode is configured to penetrate into wall tissue of a ventricle of the heart and a distance between the distal end of the elongated housing and the wall tissue of the first chamber decreases. The second electrode extends from the distal end of the elongated housing, wherein the second electrode is separate from the first electrode, wherein the second electrode is configured to be elastically deformed toward the elongate housing by the wall tissue of the atrium as a distance between the distal end of the elongated housing and the wall tissue of the atrium decreases to flexibly maintain contact with the wall tissue of the atrium without penetration of the wall tissue of the atrium by the second electrode, and wherein the second electrode is more peripheral than the first electrode relative to the longitudinal axis. The signal generation circuitry is within the elongated housing, coupled to the first electrode and the second electrode, and is configured to deliver cardiac pacing to the ventricle via the first electrode and the atrium via the second electrode.

This summary is intended to provide an overview of the subject matter described in this disclosure. It is not intended to provide an exclusive or exhaustive explanation of the methods and systems described in detail within the accompanying drawings and description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

DETAILED DESCRIPTION

In general, this disclosure is directed to configurations of the electrodes of implantable medical devices (IMDs) having housings sized for implantation wholly within a single chamber of the heart. More particularly, this disclosure is directed to configurations of electrodes that allow a single device implanted in one chamber to sense in and/or deliver cardiac pacing to more than one chamber. In some examples, in addition to an electrode configured to penetrate into tissue of another chamber, the IMD may include a flexible electrode, such as a spring-based electrode, configured to maintain contact with tissue of the chamber in which the IMD is implanted without penetrating the tissue.

Figure 1:
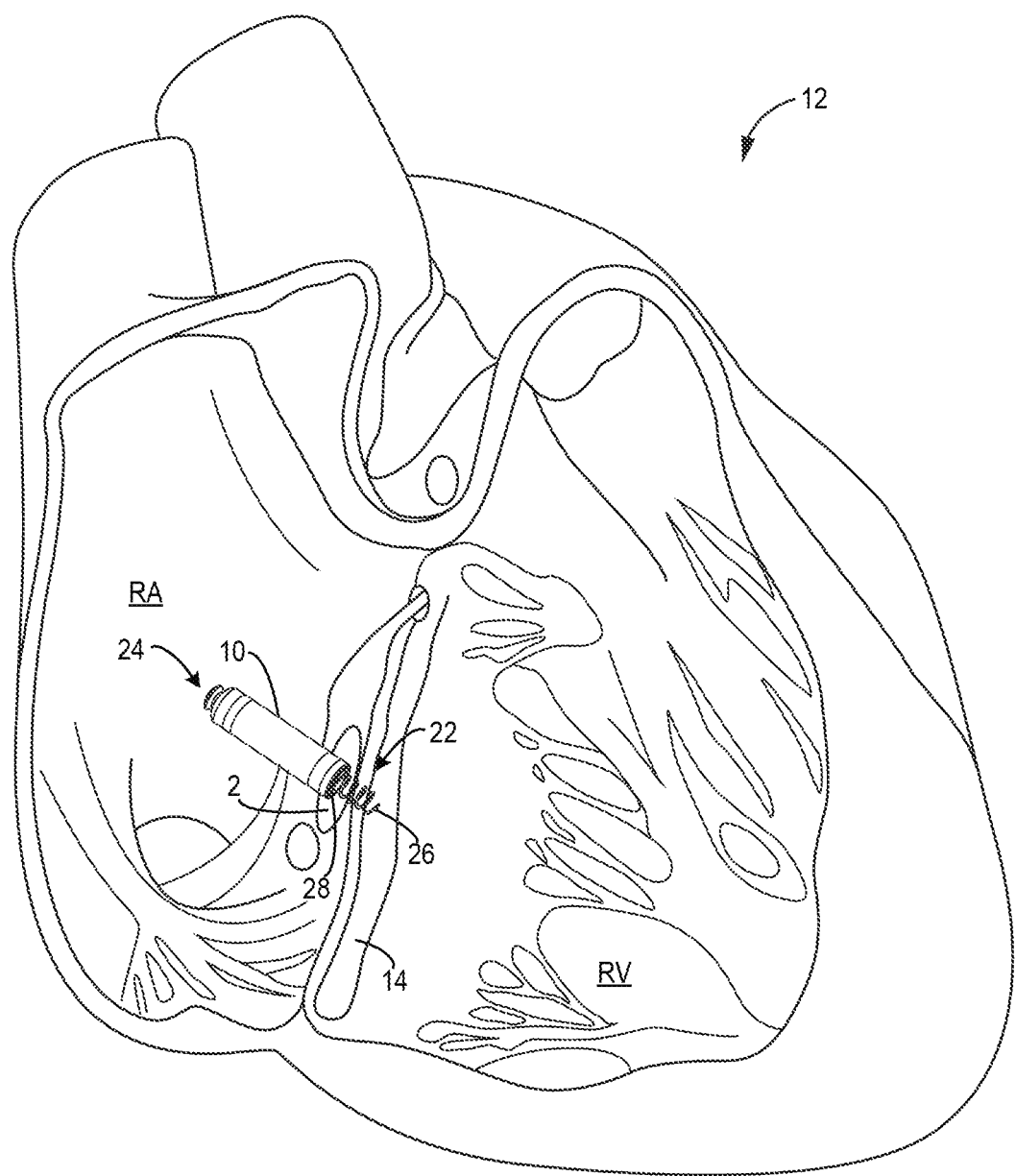
FIG. 1 is a conceptual drawing illustrating an example device implanted in the heart of a patient, in accordance with one or more aspects of this disclosure.

FIG. 1 is a conceptual drawing illustrating an example device 10 implanted in the heart 12 of a patient, in accordance with one or more aspects of this disclosure. Device 10 is shown implanted in the right atrium (RA) of the patient's heart 12 in a target implant region 2, such as triangle of Koch, in heart 12 of the patient with a distal end of device 10 directed toward the left ventricle (LV) of the patient's heart 12. Although in the example of FIG. 1 the distal end of device 10 is directed toward the LV, the distal end may be directed to other targets, such as interventricular septum of heart 12, in some examples. Target implant region 2 may lie between the bundle of His and the coronary sinus and may be adjacent the tricuspid valve.

Device 10 includes a distal end 22 and a proximal end 24. Distal end 22 includes a first electrode 26 and a second electrode 28. First electrode 26 extends from distal end 22 and may penetrate through the wall tissue of a first chamber (e.g., the RA in the illustrated example) into wall tissue of a second chamber (e.g., the LV in the illustrated example). Second electrode 28 extends from distal end 22 and is configured to flexibly maintain contact with the wall tissue of the first chamber without penetration of the wall tissue of the first chamber by the second electrode.

The configuration of electrodes 26 and 28 illustrated in FIG. 1 allows device 10 to sense cardiac signals and/or deliver cardiac pacing to multiple chambers of heart 12, e.g., the RA and ventricles in the illustrated example. In this manner, the configuration of electrodes 26 and 28 may facilitate the delivery of A-V synchronous pacing by single device 10 implanted within the single chamber, e.g., the RA. While device 10 is implanted at target implant region 2 to sense in and/or pace the RA and ventricles in the example shown in FIG. 1, a device having an electrode configuration in accordance with the examples of this disclosure may be implanted at any of a variety of locations to sense in and/or pace any two or more chambers of heart 12. For example, device 10 may be implanted at region 2 or another region, and first electrode 26 may extend into tissue, e.g., myocardial tissue, of the LV or interventricular septum to, for example, facilitate the delivery of A-V synchronous pacing. Furthermore, a device having an electrode configuration in accordance with the examples of this disclosure may be implanted at any of a variety of locations within a patient for sensing and/or delivery of therapy to other patient tissue.

Figure 2:
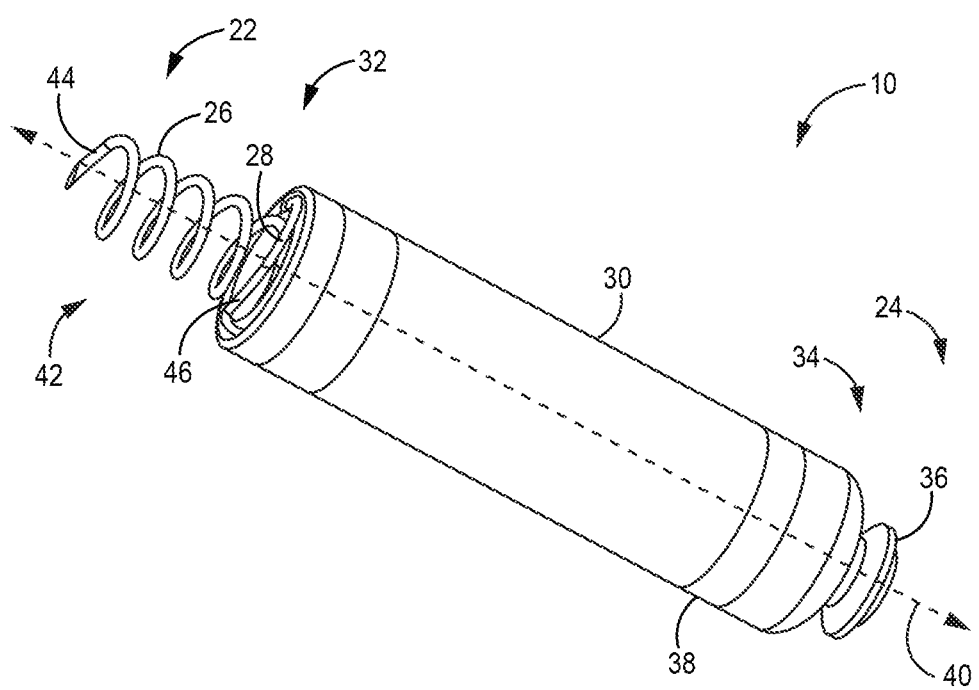
FIG. 2 is a perspective drawing illustrating the example device of FIG. 1, in accordance with one or more aspects of this disclosure.

FIG. 2 is a perspective drawing illustrating device 10. Device 10 includes a housing 30 that defines a hermetically sealed internal cavity. Housing 30 may be formed from a conductive material including titanium or titanium alloy, stainless steel, MP35N (a non-magnetic nickel-cobalt-chromium-molybdenum alloy), platinum alloy or other biocompatible metal or metal alloy, or other suitable conductive material. In some examples, housing 30 is formed from a non-conductive material including ceramic, glass, sapphire, silicone, polyurethane, epoxy, acetyl co-polymer plastics, polyether ether ketone (PEEK), a liquid crystal polymer, other biocompatible polymer, or other suitable non-conductive material.

Housing 30 extends between distal end 32 and proximal end 34. In some examples, housing can be cylindrical or substantially cylindrical but may be other shapes, e.g., prismatic or other geometric shapes. Housing 30 may include a delivery tool interface member 36, e.g., at proximal end 24, for engaging with a delivery tool during implantation of device 10.

All, substantially all, or a portion of housing 30 may function as an electrode 38, e.g., an anode, during pacing and/or sensing. In some examples, electrode 38 can circumscribe a portion of housing 30 at or near proximal end 34. Electrode 38 can fully or partially circumscribe housing 30. FIG. 2 shows electrode 38 extending as a singular band. Electrode 38 can also include multiple segments spaced a distance apart along a longitudinal axis 40 of housing 30 and/or around a perimeter of housing 30.

When housing 30 is formed from a conductive material, such as a titanium alloy, portions of housing 30 may be electrically insulated by a non-conductive material, such as a coating of parylene, polyurethane, silicone, epoxy or other biocompatible polymer, or other suitable material. For the portions of housing 30 without the non-conductive material, one or more discrete areas of housing 30 with conductive material can be exposed to define electrode 38.

When housing 30 is formed from a non-conductive material, such as a ceramic, glass or polymer material, an electrically-conductive coating or layer, such as a titanium, platinum, stainless steel, alloys thereof, a conductive material may be applied to one or more discrete areas of housing 30 to form electrode 38.

In some examples, electrode 38 may be a component, such as a ring electrode, that is mounted or assembled onto housing 30. Electrode 38 may be electrically coupled to internal circuitry of device 10 via electrically-conductive housing 30 or an electrical conductor when housing 30 is a non-conductive material. In some examples, electrode 38 is located proximate to proximal end 24 of housing 30 and can be referred to as a proximal housing-based electrode. Electrode 38 can also be located at other positions along housing 30, e.g., located proximately to distal end 22 or at other positions along longitudinal axis 40.

Each of first electrode 26 and second electrode 28 extends from a first end that is fixedly attached to housing 30 at or near distal end 22, to a second end that, in the example of FIG. 2, is not attached to housing 30 other than via the first end (e.g., is a free end). First electrode 26 includes one or more coatings configured to define a first electrically active region 44 and second electrode 28 includes one or more coatings configured to define a second electrically active region 46. In some examples, first electrically active region 44 can be more proximate to the second, e.g., distal, end of first electrode 26 than second electrically active region 46 is proximate to either end of second electrode 28. In the example of FIG. 2, first electrically active region 44 includes the distal end of electrode 26.

First and second electrodes 26 and 28 may be formed of an electrically conductive material, such as titanium, platinum, iridium, tantalum, or alloys thereof. First and second electrodes 26 and 28 may be coated with an electrically insulating coating, e.g., a parylene, polyurethane, silicone, epoxy, or other insulating coating, to reduce the electrically conductive active surface area of first and second electrodes 26 and 28, and thereby define first and second electrically active regions 44 and 46. Defining first and second electrically active regions 44 and 46 by covering portions with an insulating coating may increase the electrical impedance of first and second electrodes 26 and 28 and thereby reduce the current delivered during a pacing pulse that captures the cardiac tissue. A lower current drain conserves the power source, e.g., one or more rechargeable or non-rechargeable batteries, of device 10.

In some examples, first and second electrodes 26 and 28 may have an electrically conducting material coating on first and second electrically active regions 44 and 46 to define the active regions. For example, first and second electrically active regions 44 and 46 may be coated with titanium nitride (TiN). First and second electrodes 26 and 28 may be made of substantially similar material or may be made of different material from one another.

In the example of FIG. 2, first electrode 26 takes the form of a helix. In some examples, a helix is an object having a three-dimensional shape like that of a wire wound uniformly in a single layer around a cylindrical or conical surface such that the wire would be in a straight line if the surface were unrolled into a plane. Second electrode 28 includes a ramp portion 29 (FIG. 5C), which may be configured as a partial helix, e.g., a helix that does not make a full revolution around a circumference of the cylindrical or conical surface.

As illustrated in FIG. 2, first electrode 26 may be a right-hand wound helix, and second electrode 28 may be a left-hand wound partial helix (as shown in more detail in FIGS. 5A-G), although in other examples the handedness of the electrodes may be switched or the electrodes may have the same handedness as each other. In the example of FIG. 2, the helix and partial helix defined by first electrode 26 and second electrode 28, respectively, have the same pitch, although they may have different pitches in other examples. In some examples, one or both of electrodes 26 and 28 may have a shape other than helical. For example, the second electrode may have a loop shape (e.g., as shown in FIGS. 6A-D) in some examples. As another example, a first electrode configured to penetrate tissue of another chamber may be configured as one or more elongate darts, barbs, or tines.

First and second electrodes 26 and 28 can also vary in size and shape in order to enhance tissue contact of first and second electrically active regions 44 and 46. For example, first and second electrodes 26 and 28 can have a round cross section or could be made with a flatter cross section (e.g., oval or rectangular) based on tissue contact specifications. The size and shape of first and second electrodes 26 and 28 can also be determined by stiffness requirements. For example, stiffness requirements may vary based on the expected implantation requirements, including the tissue into which the electrodes are implanted or contact, as well as how long device 10 is intended to be implemented.

The distal end of first electrode 26 can have a conical, hemi-spherical, or slanted edge distal tip with a narrow tip diameter, e.g., less than 1 millimeter (mm), for penetrating into and through tissue layers. In some examples, the distal end of first electrode can be a sharpened or angular tip or sharpened or beveled edges, but the degree of sharpness may be constrained to avoid a cutting action that could lead to lateral displacement of the distal end of first electrode 26 and undesired tissue trauma. In some examples, first electrode 26 may have a maximum diameter at its base that interfaces with housing distal end 32. In such examples, the diameter of first electrode 26 may decrease from housing distal end 32 to the distal end of first electrode 26.

The outer dimensions of first electrode 26 can be substantially straight and cylindrical, with first electrode 26 being rigid in some examples. In some examples, first and second electrodes 26 and 28 can have flexibility in lateral directions, being non-rigid to allow some flexing with heart motion. In a relaxed state, when not subjected to any external forces, first and second electrodes 26 and 28 can be configured to maintain a distance between first and second electrically active regions 44 and 46 and housing distal end 32.

Distal end of first electrode 26 can pierce through one or more tissue layers to position first electrically active region 44 within a desired tissue layer, e.g., the ventricular myocardium or interventricular septum. Accordingly, first electrode 26 extends a distance from housing distal end 32 corresponding to the expected pacing site depth and may have a relatively high compressive strength along its longitudinal axis, which may be substantially similar to longitudinal axis 40, to resist bending in a lateral or radial direction when a longitudinal, axial, and/or rotational force is applied, e.g., to the proximal end 34 of housing 30 to advance device 10 into the tissue at target implant region 2. By resisting bending in a lateral or radial direction, first electrode 26 can maintain a spacing between a plurality of windings of first electrode 26 when first electrode 26 is a helix electrode. First electrode 26 may be longitudinally non-compressive. First electrode 26 may also be elastically deformable in lateral or radial directions when subjected to lateral or radial forces, however, to allow temporary flexing, e.g., with tissue motion, but returns to its normally straight position when lateral forces diminish. In some examples, when first electrode 26 is not exposed to any external force, or to only a force along its longitudinal axis (substantially similar to longitudinal axis 40), first electrode 26 retains a straight, linear position as shown.

In some examples, second electrode 28 or electrode 38 may be paired with first electrode 26 for sensing ventricular signals and delivering ventricular pacing pulses. In some examples, second electrode 28 may be paired with electrode 38 or first electrode 26 for sensing atrial signals and delivering pacing pulses to atrial myocardium 20 in target implant region 2. In other words, electrode 38 may be paired, at different times, with both first electrode 26 and second electrode 28 for either ventricular or atrial functionality, respectively, in some examples. In some examples, first and second electrodes 26 and 28 may be paired with each other, with different polarities, for atrial and ventricular functionality.

In some examples, second electrode 28 may be configured as an atrial cathode electrode for delivering pacing pulses to the atrial tissue at target implant region 2 in combination with electrode 38. Second electrode 28 and electrode 38 may also be used to sense atrial P-waves for use in controlling atrial pacing pulses (delivered in the absence of a sensed P-wave) and for controlling atrial-synchronized ventricular pacing pulses delivered using first electrode 26 as a cathode and electrode 38 as the return anode.

At distal end 22, device 10 includes a distal fixation assembly 42 including first electrode 26, second electrode 28, and housing distal end 32. A distal end of first electrode 26 can be configured to rest within a ventricular myocardium of the patient, and second electrode 28 can be configured to contact an atrial endocardium of the patient. In some examples, distal fixation assembly 42 can include more or less electrodes than two electrodes. In some examples, distal fixation assembly 42 may include one or more second electrodes along housing distal end 32. For example, distal fixation assembly 42 may include three electrodes configured for atrial functionality like second electrode 28, and the three electrodes may be substantially similar or different from one another. Spacing between a plurality of second electrodes 28 may be at an equal or unequal distance. Second electrode(s) 28 may be individually selectively coupled to sensing and/or pacing circuitry enclosed by housing 30 for use as an anode with first electrode 26 or as an atrial cathode electrode, or may be electrically common and not individually selectable.

Second electrode 28 is configured to flexibly maintain contact with wall tissue of the heart chamber in which device 10 is implanted, e.g., the RA endocardium, despite variations in the tissue surface or in the distance between distal end 32 of housing 30 and the tissue surface, which may occur as the wall tissue moves during the cardiac cycle.

In order to flexibly maintain contact with the wall tissue, second electrode 28 may be flexible and configured to have spring-like properties. For example, second electrode 28 may be configured to elastically deform, e.g., toward distal end 32 of housing 30, but may be spring biased toward a resting configuration and, when elastically deformed, the spring bias may urge the second electrode away from distal end 32 of housing 30. In this manner, the elastic deformation and spring bias may maintain the second electrode in consistent contact with the wall tissue of the chamber in which the device is implanted.

As described herein, to flexibly maintain contact generally refers to an electrode being moveable with respect to housing 30. For example, an electrode may be configured to elastically deform as described above. In some examples, an electrode may additionally be attached to housing 30 by, or may include, a mechanism, such as a spring or joint, that allows relative motion of the electrode to housing 30. In such examples, the electrode need not itself be deformable.

Figure 3:
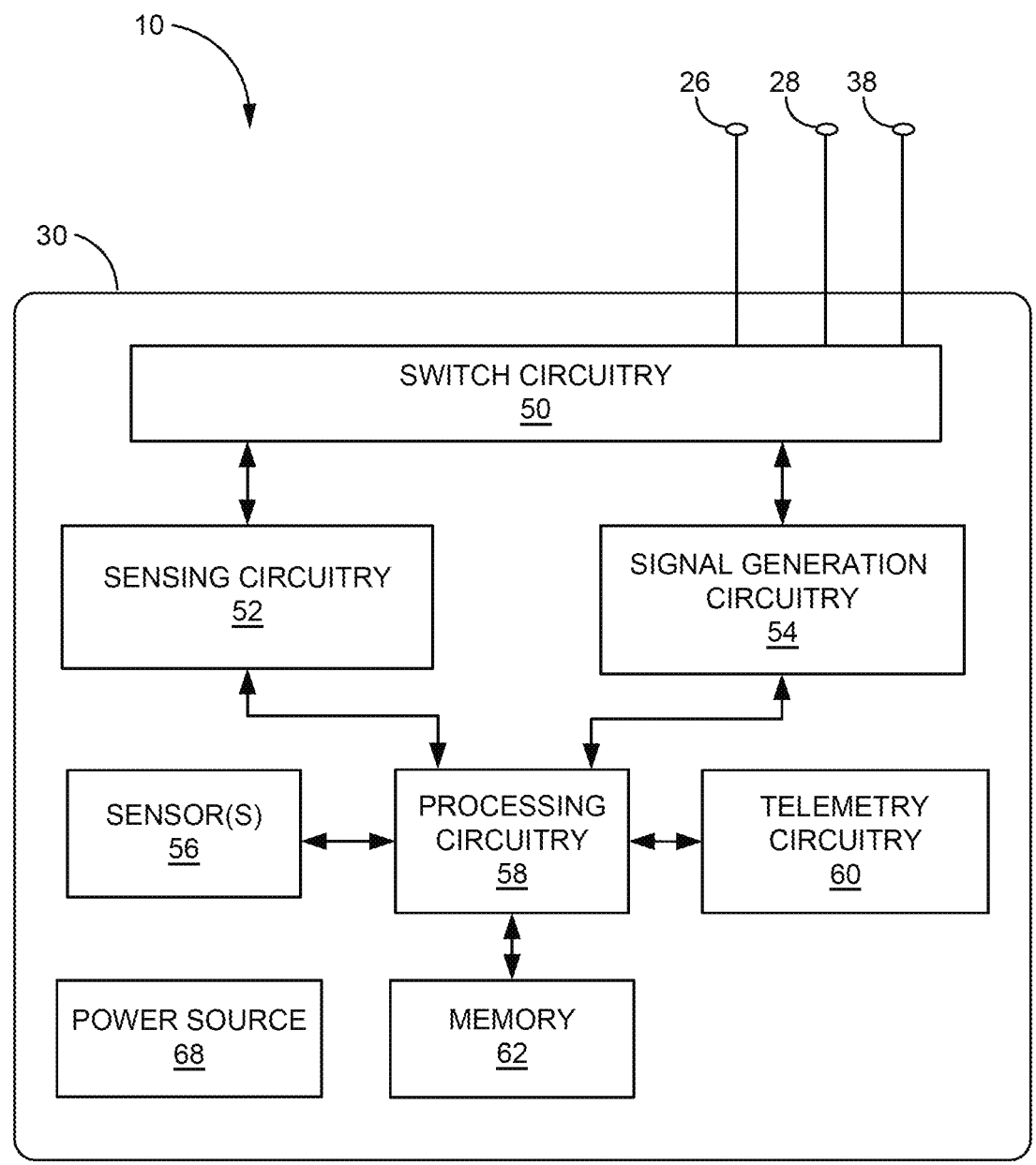
FIG. 3 is a functional block diagram illustrating an example configuration of the IMD of FIGS. 1 and 2, in accordance with one or more aspects of this disclosure.

FIG. 3 is a functional block diagram illustrating an example configuration of device 10. As illustrated in FIG. 3, device 10 include electrodes 26 and 28, which may be configured as described with respect to FIGS. 1 and 2. For example, as described with respect to FIGS. 1 and 2, first electrode 26 may be configured to extend from distal end 32 of housing 30 and may penetrate through the wall tissue of a first chamber (e.g., the RA) into wall tissue of a second chamber (e.g., the LV). Second electrode 28 extends from distal end 32 of housing 30 and is configured to flexibly maintain contact with the wall tissue of the first chamber without penetration of the wall tissue of the first chamber by the second electrode.

In the example shown in FIG. 3, device 10 includes switch circuitry 50, sensing circuitry 52, signal generation circuitry 54, sensor(s) 56, processing circuitry 58, telemetry circuitry 60, memory 62, and power source 68. The various circuitry may be, or include, programmable or fixed function circuitry configured to perform the functions attributed to respective circuitry. Memory 62 may store computer-readable instructions that, when executed by processing circuitry 58, cause device 10 to perform various functions. Memory 62 may be a storage device or other non-transitory medium. The components of device 10 illustrated in FIG. 3 may be housed within housing 30.

Signal generation circuitry 54 generates electrical stimulation signals, e.g., cardiac pacing pulses. Switch circuitry 50 is coupled to electrodes 26, 28, and 38, may include one or more switch arrays, one or more multiplexers, one or more switches (e.g., a switch matrix or other collection of switches), one or more transistors, or other electrical circuitry. Switch circuitry 50 is configured to direct stimulation signals from signal generation circuitry 54 to a selected combination of electrodes 26, 28, and 38, having selected polarities, e.g., to selectively deliver pacing pulses to the RA, ventricles, or interventricular septum of heart 12. For example, in order to pace one or both of the ventricles, switch circuitry 50 may couple first electrode 26, which has penetrated to wall tissue of a ventricle or the intraventricular septum, to signal generation circuitry 54 as a cathode, and one or both of second electrode 28 or electrode 38 to signal generation circuitry 54 as an anode. As another example, in order to pace the RA, switch circuitry 50 may couple second electrode 28, which flexibly maintains contact with the RA endocardium, to signal generation circuitry 54 as a cathode, and one or both of first electrode 26 or electrode 38 to signal generation circuitry 54 as an anode.

Switch circuitry 50 may also selectively couple sensing circuitry 52 to selected combinations of electrodes 26, 28, and 38, e.g., to selectively sense the electrical activity of either the RA or ventricles of heart 12. Sensing circuitry 52 may include filters, amplifiers, analog-to-digital converters, or other circuitry configured to sense cardiac electrical signals via electrodes 26, 28, 38. For example, switch circuitry 50 may couple each of first electrode 26 and second electrode 28 (in combination with electrode 38) to respective sensing channels provided by sensing circuitry 52 to respectively sense either ventricular or atrial cardiac electrical signals. In some examples, sensing circuitry 52 is configured to detect events, e.g., depolarizations, within the cardiac electrical signals, and provide indications thereof to processing circuitry 58. In this manner, processing circuitry 58 may determine the timing of atrial and ventricular depolarizations, and control the delivery of cardiac pacing, e.g., AV synchronized cardiac pacing, based thereon. Processing circuitry 58 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 58 herein may be embodied as firmware, hardware, software or any combination thereof.

Sensor(s) 56 may include one or more sensing elements that transduce patient physiological activity to an electrical signal to sense values of a respective patient parameter. Sensor(s) 56 may include one or more accelerometers, optical sensors, chemical sensors, temperature sensors, pressure sensors, or any other types of sensors. Sensor(s) 56 may output patient parameter values that may be used as feedback to control sensing and delivery of therapy by device 10.

Telemetry circuitry 60 supports wireless communication between device 10 and an external programmer (not shown in FIG. 3) or another computing device under the control of processing circuitry 58. Processing circuitry 58 of device 10 may receive, as updates to operational parameters from the computing device, and provide collected data, e.g., sensed heart activity or other patient parameters, via telemetry circuitry 60. Telemetry circuitry 60 may accomplish communication by radiofrequency (RF) communication techniques, e.g., via an antenna (not shown).

Power source 68 delivers operating power to various components of device 10. Power source 68 may include a rechargeable or non-rechargeable battery and a power generation circuit to produce the operating power. Recharging may be accomplished through proximal inductive interaction between an external charger and an inductive charging coil within device 10.

Figure 4:
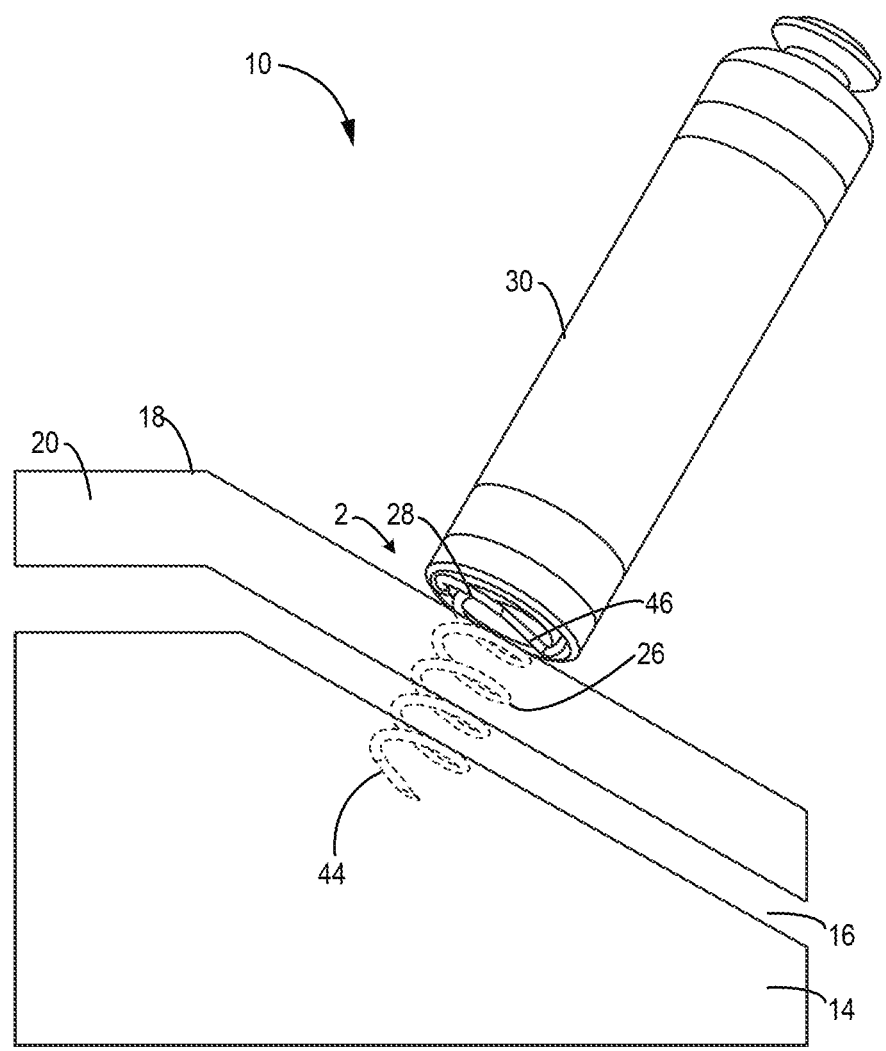
FIG. 4 is a conceptual diagram of the device of FIGS. 1-3 implanted at a target implant site.

FIG. 4 is a conceptual diagram of device 10 implanted at target implant region 2. First electrode 26 may be inserted such that tissue becomes engaged with the helix of first electrode 26. As first electrode 26 becomes engaged with tissue, first electrode 26 pierces into the tissue at target implant region 2 and advances through atrial myocardium 20 and central fibrous body 16 to position first electrically active region 44 in ventricular myocardium 14 as shown in FIG. 4. In some examples, first electrode 26 penetrates into the interventricular septum. In some examples, first electrode 26 does not perforate entirely through the ventricular endocardial or epicardial surface.

In some examples, manual pressure applied to the housing proximal end 34, e.g., via an advancement tool, provides the longitudinal force to pierce the cardiac tissue at target implant region 2. In some examples, actuation of an advancement tool rotates device 10 and first electrode 26 configured as a helix about longitudinal axis 40. The rotation of the helix about the longitudinal axis 40 advances first electrode 26 through atrial myocardium 20 and central fibrous body 16 to position first electrically active region 44 in ventricular myocardium 14 as shown in FIG. 4.

As first electrode 26 advances into the tissue, the distance between second electrode 28 and atrial endocardium 18 decreases until second electrode 28 contacts, and may press against, the surface of atrial endocardium 18 so that heart tissue becomes engaged with second electrically active region 46. Second electrode 28 is held in contact with atrial endocardium 18 by first electrode 26, e.g., retraction of second electrode 28 from the surface of atrial endocardium 18 is prevented by first electrode 26. Second electrode 28 is also configured, as described herein, to flexibly maintain contact with atrial endocardium 18. In some examples, second electrode is elastically deformable toward distal end 32 (FIG. 2) of housing 30, and has a spring bias urging second electrode distally from distal end 32. First electrode 26 can be the sole fixation feature of device 10 in some examples. The distance first electrode 26 extends from housing 30 can be selected so first electrically active region 44 reaches an appropriate depth in the tissue layers to reach the targeted pacing and sensing site, in this case in ventricular myocardium 14, without puncturing all the way through into an adjacent cardiac chamber.

Target implant region 2 in some pacing applications is along atrial endocardium 18, substantially inferior to the AV node and bundle of His. First electrode 26 can have a length that penetrates through atrial endocardium 18 in target implant region 2, through the central fibrous body 16 and into ventricular myocardium 14 without perforating through the ventricular endocardial surface. In some examples, when the full length of first electrode 26 is fully advanced into target implant region 2, first electrically active region 44 rests within ventricular myocardium 14 and second electrode 28 is positioned in intimate contact with atrial endocardium 18. First electrode 26 may extend from housing distal end 32 approximately 3 mm to 12 mm in various examples. In some examples, first electrode 26 may extend a distance from housing 30 of at least 3 millimeters (mm), at least 3 mm but less than 20 mm, less than 15 mm, less than 10 mm, or less than 8 mm in various examples. The diameter of first and second electrodes 26 and 28 may be less than 2 mm and may be 1 mm or less, or even 0.6 mm or less.

Figure 5A:
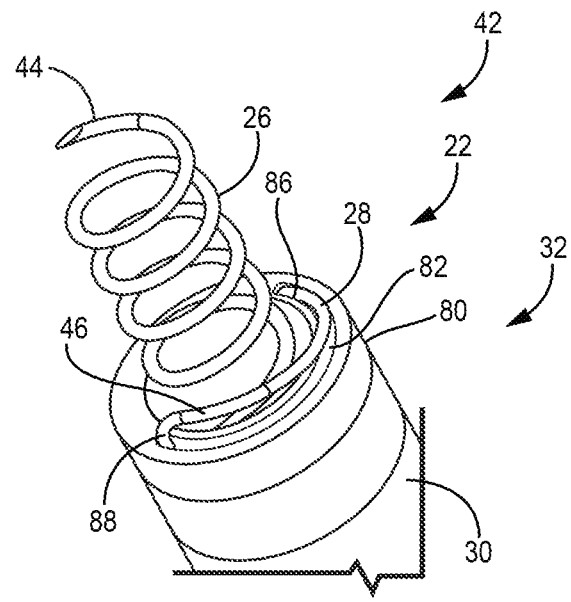
FIGS. 5A, 5B, 5C, and 5D are partial views of the device of FIGS. 1-4 from different perspectives, in accordance with one or more aspects of this disclosure.

FIGS. 5A, 5B, 5C, and 5D are partial views of device 10 from different perspectives. FIG. 5A is a partial view of distal end 22 of device 10 including distal fixation assembly 42. Housing 30 includes a header 80. In some examples, header 80 may be separate or integral with housing 30 and can be made of the same or different materials as housing 30. Housing distal end 32, e.g., header 80, defines a recess 82 (e.g., a recessed channel) to receive at least a portion of second electrode 28 as it is elastically deformed toward housing 30. Second electrically active region 46 can maintain contact with the tissue surface when second electrode 28 is partially or fully deformed into recess 82.

In some examples, second electrode 28 can maintain contact with tissue as the extent of deformation of second electrode 28 toward housing 30 varies. Second electrode 28 may be spring biased to an undeformed position, and deformation of second electrode 28 proximally toward distal end 32 of housing 30 may result in a spring force directed distally from housing 30 that urges second electrode 28, and more particularly second electrically active region 46, against cardiac tissue. For example, deformation of second electrode 28 may vary with the motion of the heart. Because, at least in part, of the ability of the deformation of second electrode 28 to vary, e.g., during the cardiac cycle, second electrically active region 46 can maintain consistent contact with the tissue and provide pacing to the heart.

Figure 5B:
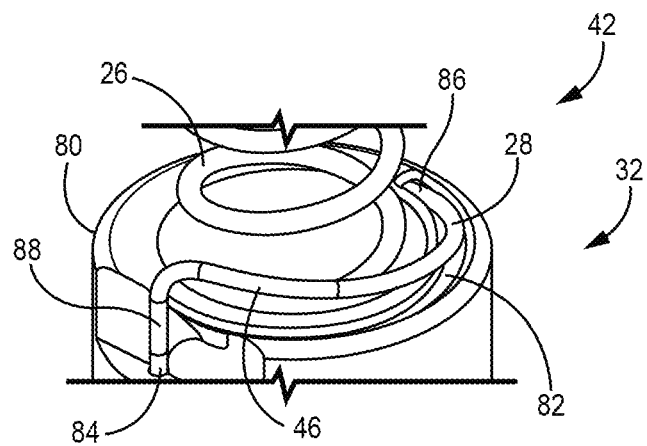
Figure 5C:
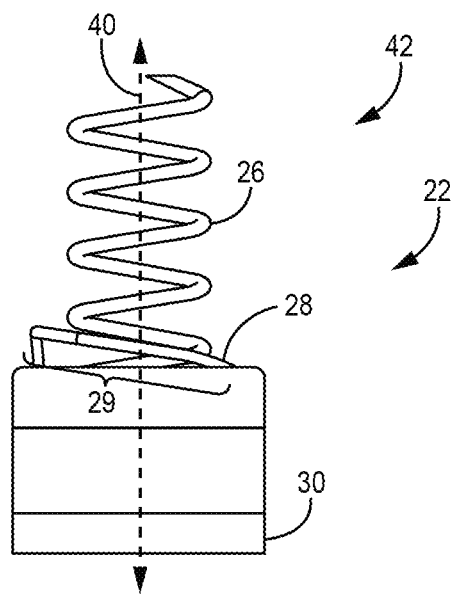
Figure 5D:
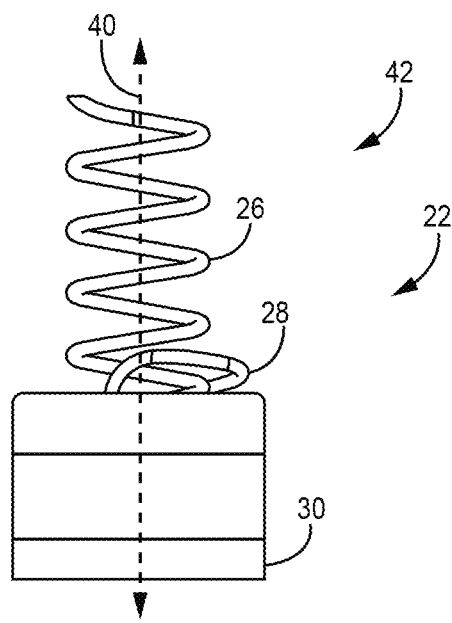

FIG. 5B is a conceptual diagram of a partial view of device 10 with a cut-away to show a recessed hole 84, in accordance with one or more aspects of this disclosure. FIGS. 5C and 5D are conceptual diagrams of a partial, side perspective view of device 10, in accordance with one or more aspects of this disclosure. As illustrated in FIG. 5B, an attached end 86 of second electrode 28 is attached to header 80 and is connected (e.g., electrically) to a feedthrough. At the opposite end of second electrode 28, a free-floating end 88 of second electrode 28 is bent back towards device 10 and is able to move into recessed hole 84 as second electrode 28 is deformed. For example, second electrically active region 46 can maintain contact with tissue while free-floating end 88 is pushed into recessed hole 84 due to deformation of second electrode 28 with heart motion.

As discussed herein, first electrode 26 and second electrode 28 can have different handed helical shapes. For example, the helix of first electrode 26 can be a right-hand helix. First electrode 26 can be inserted, e.g., in a manner similar to rotating and advancing a threaded screw, such that tissue becomes engaged with the helix of first electrode 26. The partial helix of second electrode 28 can be a left-hand helix. As the distance between second electrode 28 and the tissue decreases due to right-hand rotation of first electrode 26, the tissue will gradually contact ramp portion 29 (illustrated in FIG. 5C) of second electrode 28 similar to advancing along a ramp, and the ramp-shape of ramp portion 29 will gradually deform, e.g., compress, toward housing 30.

Due to this configuration of second electrode 28, in some examples, having first electrode 26 and second electrode 28 be the same handedness could present tissue-insertion difficulties. For example, if second electrode 28 were also right-hand wound, the blunter end (shown to the left side of ramp portion 29 in FIG. 5C) would be the first to contact endocardial tissue. The blunt-end of second electrode 28 could catch on tissue and restrict rotation, instead of a ramp being gradually deformed towards housing 30. The restriction of rotation for second electrode 28 could decrease the contact between second electrically active region 46 and the tissue of the patient's heart 12.

In some examples, first electrode 26 includes a helix with a first pitch, and ramp portion 29 of second electrode 28 is a partial helix with a second pitch. A first pitch of the helix of first electrode 26 can be the same, substantially similar, or different than the second pitch of the partial helix of second electrode 28. In some examples, second electrode 28 can be more peripheral than first electrode 26 relative to longitudinal axis 40. In some examples, first electrode 26 resides in an inner space defined by second electrode 28 and is approximately concentric with second electrode 28.

Figure 5E:
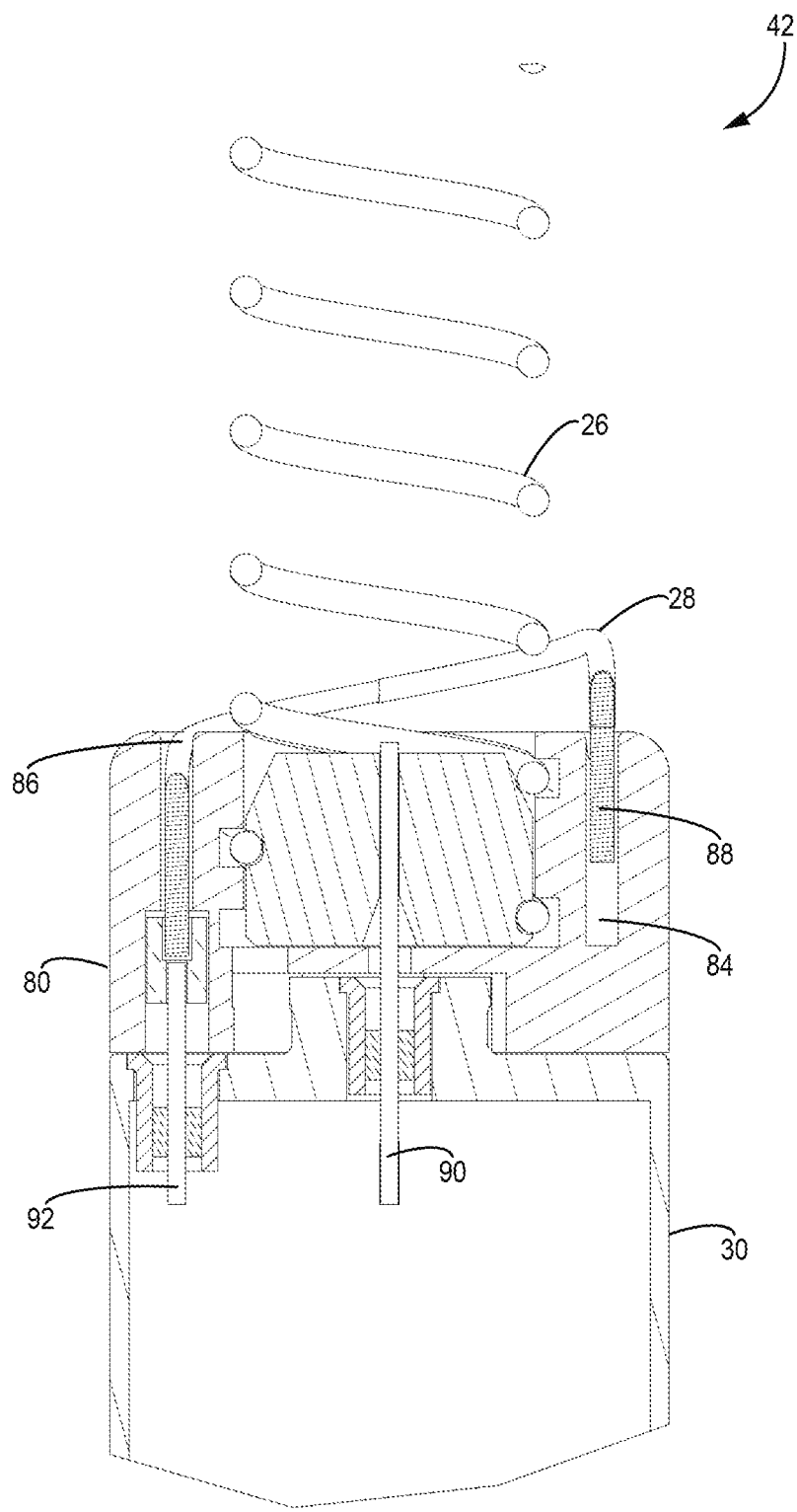
FIG. 5E is a cross-sectional view of the device of FIGS. 1-4, the cross-section taken along the longitudinal axis of the device, in accordance with one or more aspects of this disclosure.

FIG. 5E is a conceptual drawing illustrating a cross-sectional view of device 10 taken along its longitudinal axis, in accordance with one or more aspects of this disclosure. FIG. 5E illustrates distal fixation assembly 42 including first electrode 26, second electrode 28, header 80 with recessed hole 84, and housing 30. First electrode 26 is connected (e.g., electrically) to a first feedthrough 90. Attached end 86 of second electrode 28 is connected (e.g., electrically) to a second feedthrough 92. At the opposite end of second electrode 28, free-floating end 88 of second electrode 28 is able to be compressed by deformation into recessed hole 84. First feedthrough 90 and second feedthrough 92 are electrically coupled to circuitry within housing 30, such as switch circuitry 50, sensing circuitry 52, and/or signal generation circuitry 54 (FIG. 3).

Figure 5F:
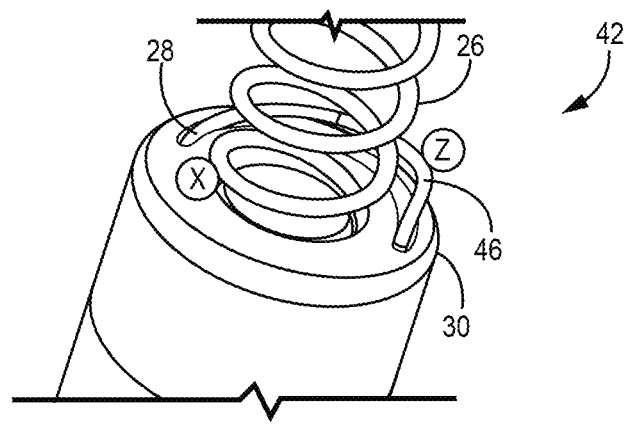
FIG. 5F is a partial view, and FIG. 5G an end view of the device of FIGS. 1-4, in accordance with one or more aspects of this disclosure.
Figure 5G:
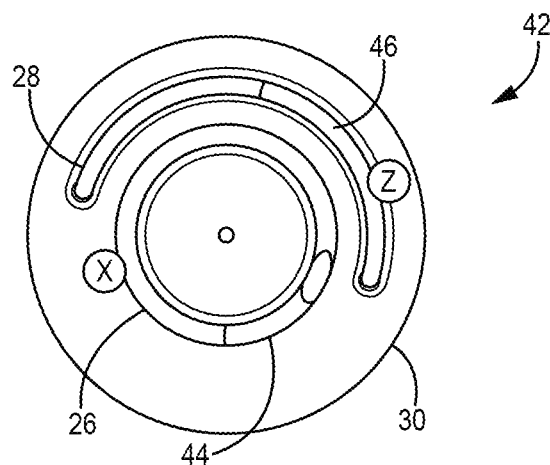

FIG. 5F is a partial view, and FIG. 5G is an end view of device 10, in accordance with one or more aspects of this disclosure. In some examples, first electrode 26 may injure an insertion area, generally indicated by the "X" in FIGS. 5F and 5G, where first electrode 26 enters the tissue, e.g., first electrode 26 may injure the endocardial tissue of the atrium where first electrode 26 penetrates. As first electrode 26 advances into the tissue of the patient, insertion area X where first electrode 26 penetrated may eventually be located at the intersection of first electrode 26 and housing 30. In some examples, second electrode 28 may be configured and positioned on device 10 such that second electrically active region 46 is positioned away from insertion area X, e.g., as far away from insertion area X as possible. In some examples, a portion Z of second electrically active region 46 of second electrode 28 that contacts patient tissue, or longitudinal midpoint of second electrically active region 46, may be located approximately 180°, i.e., opposite, from insertion area X relative to the longitudinal axis of device 10 and first electrode 26. In some examples, how far first electrode 26 is inserted into the tissue may depend, at least in part, on the relative positioning of areas X and Z.

In some examples, the dimensions such as size and shape, e.g., length of coil, number of windings, spacing between windings, and size and shape of the electrically active regions, of first electrode 26 and second electrode 28 may be determined, at least in part, on the relative positioning of areas X and Z. For example, dimensions of first electrode 26 and second electrode 28 and their attachment to housing 30 may be selected such that insertion area X is opposite or substantially opposite from area Z of second electrically active region 46.

Figure 6A:
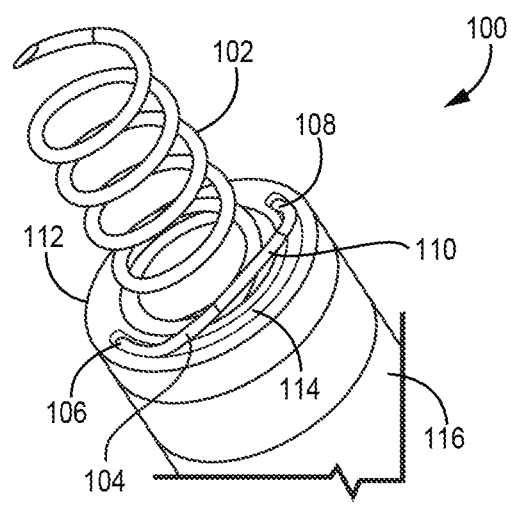
FIGS. 6A, 6B, 6C, and 6D are partial views of another example device from different perspectives, in accordance with one or more aspects of this disclosure.
Figure 6B:
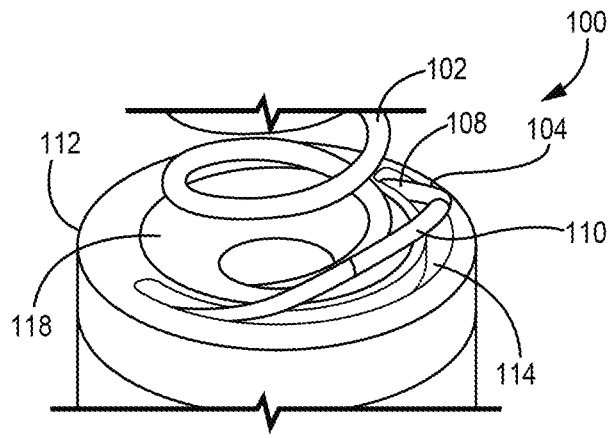
Figure 6C:
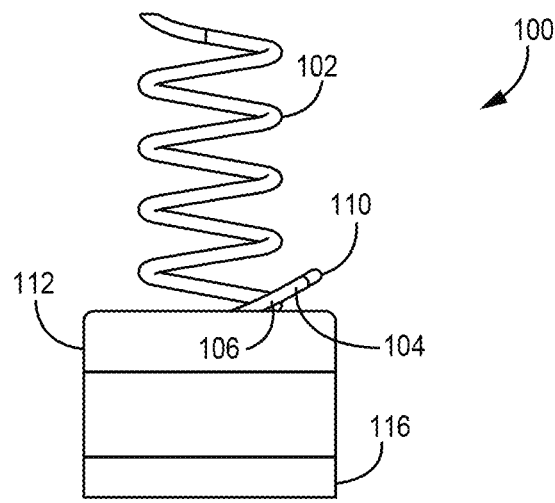
Figure 6D:
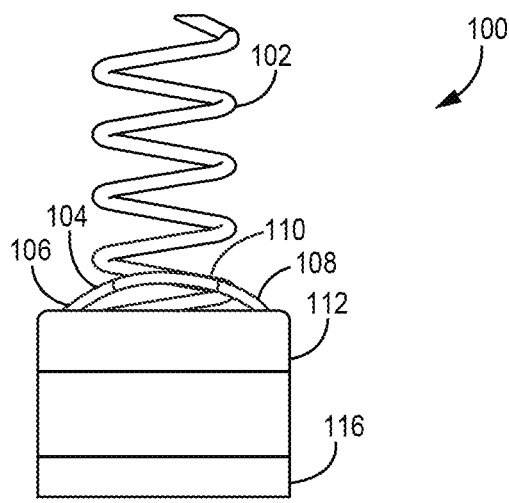

FIGS. 6A, 6B, 6C, and 6D are diagrams of partial views of a distal fixation assembly 100 of another example device from different perspectives, in accordance with one or more aspects of this disclosure. FIGS. 6A and 6B offer top perspective views, and FIGS. 6C and 6D offer side perspective views. Distal fixation assembly 100 may be the same or substantially similar to distal fixation assembly 42, except for the differences described herein. Distal fixation assembly 100 includes a first electrode 102, a second electrode 104, and a housing 116. Second electrode 104 extends from a first end 106 to a second end 108 with an electrically active region 110 between first end 106 and second end 108. Housing 116 includes a header 112 with a recess 114 (e.g., a recessed channel) to receive second electrode 104. First and second ends 106 and 108 are attached (e.g., anchored) to housing 116. Either (or both of) first or second end 106 and 108 is connected (e.g., electrically) to a feedthrough. As tissue contact deforms second electrode 104, recess 114 receives second electrode 104. Electrically active region 110 of second electrode 104 will remain in contact with tissue while the other portions of second electrode 104 extending from first and second ends 106 and 108 are pushed into recess 114.

Figure 7:
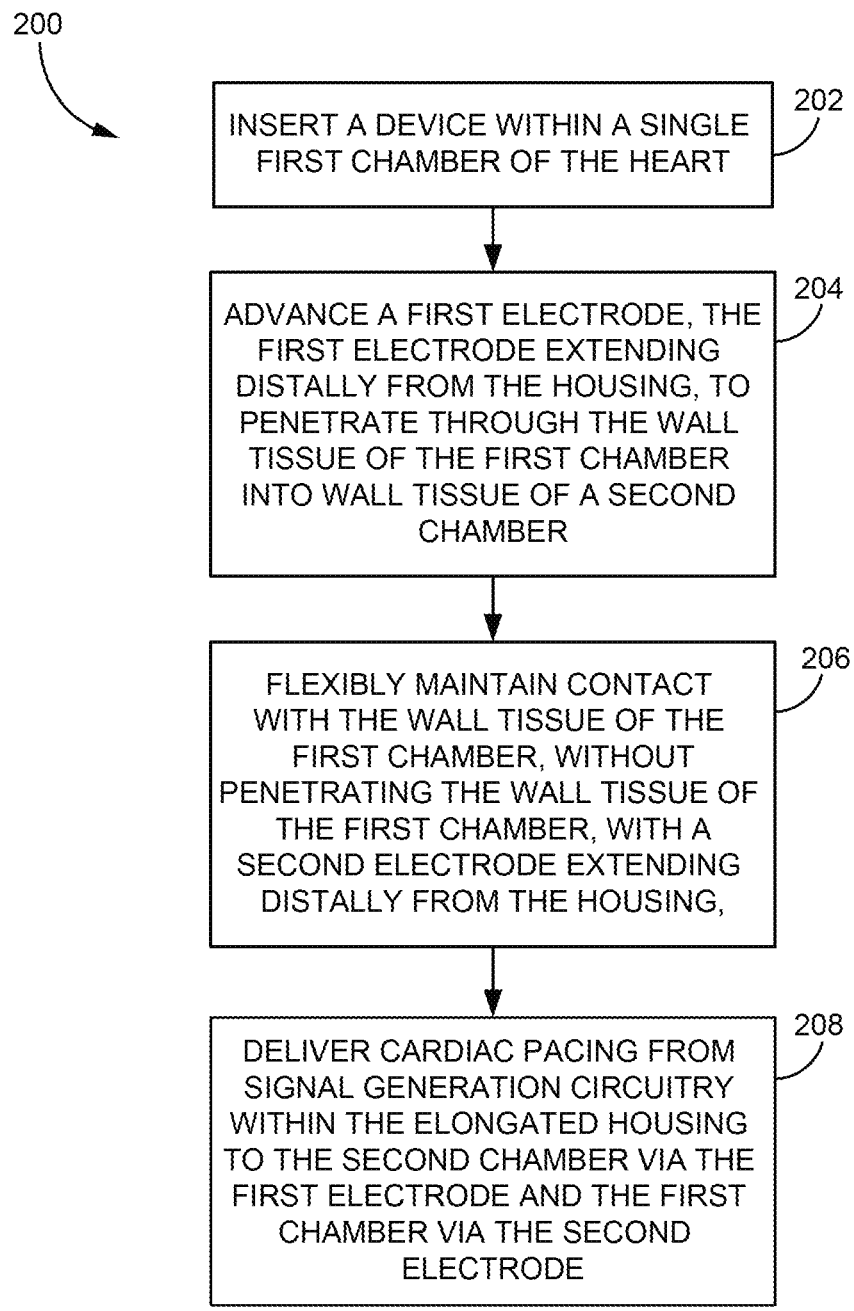
FIG. 7 is a flow diagram of an example technique for deploying a device having electrodes configured according to one or more aspects of this disclosure.

FIG. 7 is a flow diagram of an example method 200 for deploying the device. The technique of FIG. 7 will be described with concurrent reference to device 10 (FIG. 1) although a person having ordinary skill in the art will understand that the technique may be performed in reference to another implantable medical lead or other medical device.

According to example method 200 of FIG. 7, a device 10 including an elongated housing 30, extending from a proximal end of the housing to a distal end of the housing, is inserted within a single first chamber of the heart, the first chamber having wall tissue (202). First electrode 26 is advanced to penetrate through the wall tissue of the first chamber into wall tissue of a second chamber, e.g., by rotation of device 10 and first electrode 26 about longitudinal axis 40, with first electrode 26 extending distally from the distal end 32 of elongated housing 30 through the wall tissue of the first chamber into wall tissue of a second chamber (204). In some examples, advancing first electrode 26 includes positioning a distal end of first electrode 26 within a ventricular myocardium of the patient.

Second electrode 28 extends from distal end 32 of elongated housing 30, flexibly maintaining contact with the wall tissue of the first chamber, without penetrating the wall tissue of the first chamber (206). In some examples, flexibly maintaining contact with the wall tissue of the first chamber with second electrode 28 includes contacting atrial endocardium 18 of the patient. In some examples, flexibly maintaining contact with the wall tissue of the first chamber with second electrode 28 includes deforming second electrode 28 toward elongated housing 30 by the wall tissue of the first chamber as a distance between the distal end of elongated housing 30 and the wall tissue of the first chamber decreases. In some examples, recess 82 receives at least a portion of second electrode 28 as it is elastically deformed back toward elongated housing 30. In some examples, a spring bias of second electrode 28 urges second electrode 28 away from housing and into consistent contact with the wall tissue of the first chamber. Example method 200 further comprises delivering cardiac pacing from signal generation circuitry 54 within elongated housing 30 to the second chamber via first electrode 26 and the first chamber via second electrode 28 (208).

Inflammation of patient tissue may result from interaction with the IMD. For example penetration of tissue by a first electrode and/or contact between tissue and the second electrode may result in inflammation of the tissue. Inflammation of patient tissue proximate to electrodes may result in higher thresholds for stimulation delivered to the tissue to activate, or capture, the tissue. Higher capture thresholds may, in turn, increase the consumption of a power source of the IMD associated with delivery of the stimulation.

In some examples, an IMD as described herein, such as IMDs 10, 42, and 100, may include one or more steroid eluting elements. The steroid may mitigate inflammation of patient tissue resulting from interaction with the IMD. The steroid eluting element(s) may be configured to elute one or more steroids to tissue in proximity to the element(s) over time. In some examples, the one or more steroid eluting elements comprise one or more monolithic controlled release devices (MCRDs).

In some examples, an IMD includes one or both of a first steroid eluting element configured to elute one or more steroids to tissue proximate to the first electrode, and a second steroid eluting element configured to elute one or more steroids to tissue proximate to the second electrode. For example, as illustrated in FIG. 6B, IMD 100 includes a steroid eluting element 118 at a distal end of housing 116, e.g., included with, attached to, or formed on header 112. Steroid eluting element 118 is configured to elute one or more steroids to tissue proximate to second electrode 104.

Figure 8:
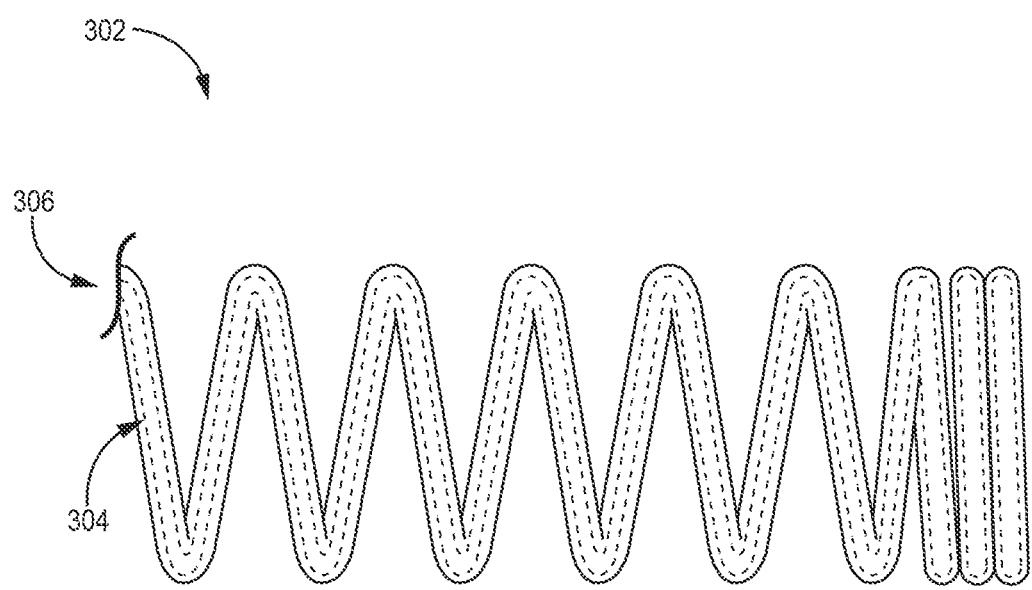
FIG. 8 illustrates an example first electrode that includes a steroid eluting element.

FIG. 8 illustrates an example first electrode 302 that includes a steroid eluting element 304. Steroid eluting element 304 is configured to elute one or more steroids to tissue proximate to first electrode 302. In the illustrated example, steroid eluting element 304 is disposed within a channel or lumen of first electrode 302. The steroid may elute through a distal opening 306 of the channel or lumen. In some examples, first electrode 302 may be porous, and the steroid may additionally or alternatively elute through the pores. In some examples, steroid eluting element 304 may additionally or alternatively be formed on an outer surface of first electrode 302.

Figure 9B:
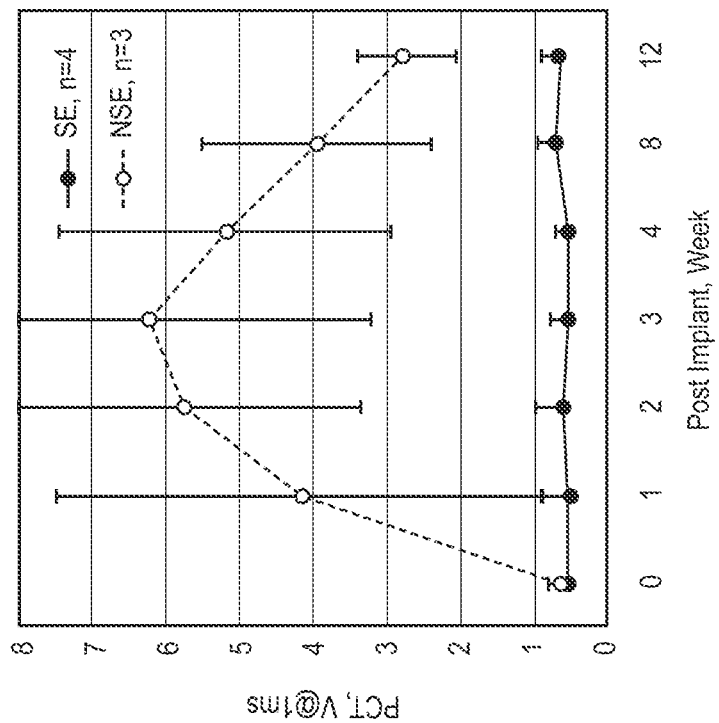
FIGS. 9A and 9B illustrate data from experiments in which IMDs having first and second electrodes were implanted within right atria as described herein.
Figure 9A:
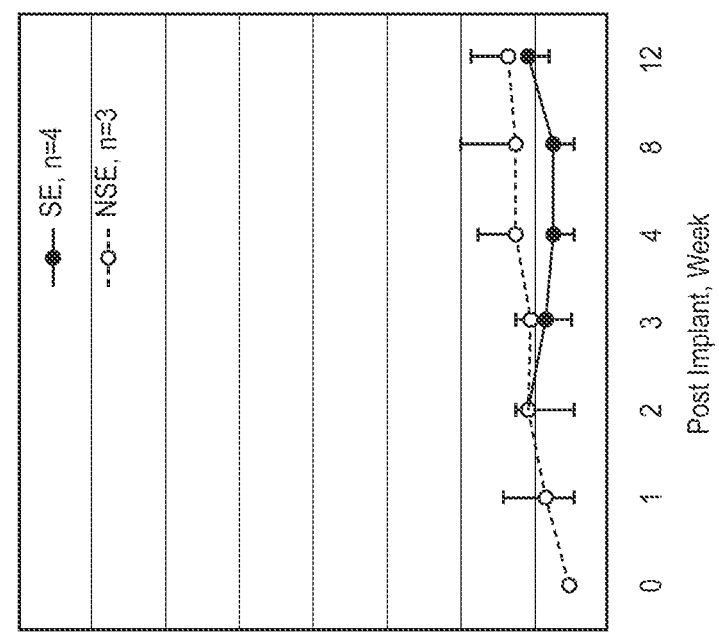

FIGS. 9A and 9B illustrate data from experiments in which IMDs having first and second electrodes were implanted within right atria as described herein. More particularly, FIG. 9A illustrates capture thresholds over time for first electrodes, some having a steroid eluting element (SE) and some lacking a steroid eluting element (NSE), that penetrate the ventricular myocardium. FIG. 9B illustrates capture thresholds over time for second electrodes, some having a steroid eluting element (SE) and some lacking a steroid eluting element (NSE), that contact the atrial endocardium. As can be seen from FIGS. 9A and 9B, steroid eluting elements may limit increases in capture threshold over time that may otherwise occur for electrodes lacking steroid eluting elements. Such increases may be more dramatic in second electrodes lacking steroid eluting elements that contact the atrial endocardium.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

In addition, it should be noted that system described herein may not be limited to treatment of a human patient. In alternative examples, the system may be implemented in non-human patients, e.g., primates, canines, equines, pigs, and felines. These other animals may undergo clinical or research therapies that may benefit from the subject matter of this disclosure.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Example 1: A device comprising: an elongated housing that extends from a proximal end of the housing to a distal end of the housing, the elongated housing configured to be implanted wholly within a first chamber of the heart, the first chamber of the heart having wall tissue; a first electrode extending distally from the distal end of the elongated housing, wherein a distal end of the first electrode is configured to penetrate through the wall tissue of the first chamber into wall tissue of a second chamber of the heart that is separate from the first chamber of the heart; a second electrode extending from the distal end of the elongated housing, wherein the second electrode is separate from the first electrode and wherein the second electrode is configured to flexibly maintain contact with the wall tissue of the first chamber without penetration of the wall tissue of the first chamber by the second electrode; and signal generation circuitry within the elongated housing, the signal generation circuitry coupled to the first electrode and the second electrode, wherein the signal generation circuitry is configured to deliver cardiac pacing to the second chamber via the first electrode and the first chamber via the second electrode.

Example 2: The device of example 1, wherein a distal end of the first electrode is configured to penetrate into a ventricular myocardium of the patient, and wherein the second electrode is configured to flexibly maintain contact with an atrial endocardium of the patient.

Example 3: The device of example 1 or 2, wherein the first electrode comprises a helix.

Example 4: The device of example 3, wherein the second electrode comprises a ramp portion configured as a partial helix.

Example 5: The device of example 4, wherein a first pitch of the helix of the first electrode and a second pitch of the partial helix of the second electrode are substantially similar.

Example 6: The device of example 4 or 5, wherein one of the helix of the first electrode and the partial helix of the second electrode is right-handed, and the other of the helix of the first electrode and the partial helix of the second electrode is left-handed.

Example 7: The device of any one of examples 1 to 6, wherein the elongated housing defines a longitudinal axis, and the second electrode is more peripheral than the first electrode relative to the longitudinal axis.

Example 8: The device of any one of examples 1 to 7, wherein the first electrode resides in an inner space defined by the second electrode and is substantially concentric with the second electrode.

Example 9: The device of any one of examples 1 to 8, wherein the second electrode extends from a first end to a second end, wherein the first electrode comprises one or more coatings configured to define a first electrically active region and the second electrode comprises one or more coatings configured to define a second electrically active region, and wherein the first electrically active region is more proximate to the distal end of the first electrode than the second electrically active region is proximate to either end of the second electrode.

Example 10: The device of any one of examples 1 to 9, wherein the second electrode is configured to be elastically deformed toward the elongated housing by the wall tissue of the first chamber as a distance between the distal end of the elongated housing and the wall tissue of the first chamber decreases to maintain contact with the wall tissue of the first chamber without penetration of the wall tissue of the first chamber by the second electrode.

Example 11: The device of example 10, wherein the distal end of the elongated housing defines a recess to receive at least a portion of the second electrode as the second electrode is elastically deformed toward the elongated housing.

Example 12: The device of any one of examples 1 to 3 or 7 to 11, wherein the second electrode extends from a first end to a second end, the first and second ends attached to the elongated housing.

Example 13: The device of any one of examples 1 to 11, wherein the second electrode extends from a first end attached to the elongated housing to a free second end that is bent back towards the elongated housing.

Example 14: The device of any one of examples 1 to 12, wherein a length of the first electrode is within a range from approximately 3 millimeters (mm) to approximately 12 mm.

Example 15: The device of any one of examples 1 to 14, further comprising a third electrode extending from the distal end of the elongated housing, wherein the third electrode is substantially similar to the second electrode.

Example 16: A method comprising: delivering cardiac pacing from a device to a heart, wherein the device comprises an elongated housing, extending from a proximal end of the housing to a distal end of the housing, and implanted wholly within a first chamber of the heart, the first chamber having wall tissue, wherein the device comprises: a first electrode extending distally from the distal end of the elongated housing, wherein a distal end of the first electrode penetrates through the wall tissue of the first chamber into wall tissue of a second chamber of the heart that is separate from the first chamber of the heart; and a second electrode extending from the distal end of the elongated housing, wherein the second electrode is separate from the first electrode and wherein the second electrode is configured to flexibly maintain contact with the wall tissue of the first chamber without penetration of the wall tissue of the first chamber by the second electrode, and wherein delivering the cardiac pacing comprises: delivering cardiac pacing to the second chamber via the first electrode; and delivering cardiac pacing to the first chamber via the second electrode.

Example 17: The method of example 16, wherein a distal end of the first electrode penetrates into a ventricular myocardium of the patient, and wherein the second electrode flexibly maintains contact with an atrial endocardium of the patient.

Example 18: The method of example 16 or 17, wherein the first electrode comprises a helix.

Example 19: The method of example 18, wherein the second electrode comprises a ramp portion configured as a partial helix.

Example 20: The method of example 19, wherein a first pitch of the helix of the first electrode and a second pitch of the partial helix of the second electrode are substantially similar.

Example 21: The method of example 19 or 20, wherein one of the helix of the first electrode and the partial helix of the second electrode is right-handed, and the other of the helix of the first electrode and the partial helix of the second electrode is left-handed.

Example 22: The method of any one of examples 16 to 21, wherein the elongated housing defines a longitudinal axis, and the second electrode is more peripheral than the first electrode relative to the longitudinal axis.

Example 23: The method of any one of examples 16 to 22, wherein the first electrode resides in an inner space defined by the second electrode and is substantially concentric with the second electrode.

Example 24: The method of any one of examples 16 to 23, wherein the second electrode extends from a first end to a second end, wherein the first electrode comprises one or more coatings configured to define a first electrically active region and the second electrode comprises one or more coatings configured to define a second electrically active region, and wherein the first electrically active region is more proximate to the distal end of the first electrode than the second electrically active region is proximate to either end of the second electrode.

Example 25: The method of any one of examples 16 to 24, wherein the second electrode is elastically deformed toward the elongated housing by the wall tissue of the first chamber as a distance between the distal end of the elongated housing and the wall tissue of the first chamber decreases to maintain contact with the wall tissue of the first chamber without penetration of the wall tissue of the first chamber by the second electrode.

Example 26: The method of example 25, wherein the distal end of the elongated housing defines a recess to receive at least a portion of the second electrode as it is elastically deformed toward the elongated housing.

Example 27: The method of any one of examples 16 to 18 or 22 to 26, wherein the second electrode extends from a first end to a second end, the first and second ends are attached to the elongated housing.

Example 28: The method of any one of examples 16 to 26, wherein the second electrode extends from a first end attached to the elongated housing to a free second end that is bent back towards the elongated housing.

Example 29: A device comprising: an elongated housing extending from a proximal end of the housing to a distal end of the housing and defining a longitudinal axis, the housing configured to be implanted wholly within an atrium of the heart; a first electrode extending distally from the distal end of the elongated housing and comprising a helix, wherein, as the helix is rotated about the longitudinal axis, a distal end of the first electrode is configured to penetrate through wall tissue of the atrium into wall tissue of a ventricle of the heart and a distance between the distal end of the elongated housing and the wall tissue of the first chamber decreases; a second electrode extending from the distal end of the elongated housing, wherein the second electrode is separate from the first electrode, wherein the second electrode is configured to be elastically deformed toward the elongate housing by the wall tissue of the atrium as a distance between the distal end of the elongated housing and the wall tissue of the atrium decreases to flexibly maintain contact with the wall tissue of the atrium without penetration of the wall tissue of the atrium by the second electrode, and wherein the second electrode is more peripheral than the first electrode relative to the longitudinal axis; and signal generation circuitry within the elongated housing, the signal generation circuitry coupled to the first electrode and the second electrode, wherein the signal generation circuitry is configured to deliver cardiac pacing to the ventricle via the first electrode and the atrium via the second electrode.

Various examples have been described. These and other examples are within the scope of the following claims.

What is claimed is:

1. A device comprising:
   an elongated housing extending from a proximal end of the housing to a distal end of the housing and defining a longitudinal axis, the housing configured to be implanted wholly within a first chamber of the heart;
   a first electrode extending distally from the distal end of the elongated housing and comprising a helix, wherein, as the helix is rotated about the longitudinal axis, a distal end of the first electrode is configured to penetrate wall tissue of the first chamber and into wall tissue of a second chamber of the heart as a distance between the distal end of the elongated housing and the wall tissue of the first chamber decreases;
   a second electrode extending from the distal end of the elongated housing, wherein the second electrode is separate from the first electrode, wherein the second electrode is configured to maintain contact with the wall tissue of the first chamber without penetration of the wall tissue of the first chamber by the second electrode as a distance between the distal end of the elongated housing and the wall tissue of the first chamber decreases, and wherein the second electrode is configured as a partial helix; and
   signal generation circuitry within the elongated housing, the signal generation circuitry coupled to the first electrode and the second electrode, wherein the signal generation circuitry is configured to deliver cardiac pacing to the second chamber via the first electrode and the first chamber via the second electrode.

2. The device of claim 1, wherein the distal end of the first electrode is configured to penetrate into a ventricular myocardium of the patient and wherein the second electrode is configured to flexibly maintain contact with an atrial endocardium of the patient.

3. The device of claim 1, wherein a first pitch of the helix of the first electrode and a second pitch of the partial helix of the second electrode are substantially similar.

4. The device of claim 1, wherein the helix of the first electrode and the partial helix of the second electrode are wound in a same direction.

5. The device of claim 1, wherein the helix of the first electrode and the partial helix of the second electrode are wound in different directions.

6. The device of claim 1, wherein the second electrode is peripheral to the first electrode relative to the longitudinal axis.

7. The device of claim 1, wherein the second electrode extends from a first end to a second end, wherein the first electrode comprises one or more coatings configured to define a first electrically active region and the second electrode comprises one or more coatings configured to define a second electrically active region, and wherein the first electrically active region is more distal from the distal end of the elongated housing than the second electrically active region.

8. The device of claim 7, wherein the second end of the second electrode is a free floating end.

9. The device of claim 1, further comprising at least one steroid eluting element configured to elute a steroid proximate to at least one of the first electrode or the second electrode.

10. The device of claim 1, wherein the first chamber comprises an atrium of the heart and wherein the second chamber comprises a ventricle of the heart.

11. A method comprising:
implanting a device wholly within a first chamber of the heart by causing a distal end of a first electrode extending distally from a distal end of an elongated housing of the device to penetrate wall tissue of the first chamber of the heart, wherein the first electrode comprises a helix;
advancing the distal end of the first electrode into wall tissue of a second chamber of the heart and placing a second electrode extending from the distal end of the elongated housing in contact with the wall tissue of the first chamber of the heart without penetration of the wall tissue of the first chamber by the second electrode, wherein the second electrode is configured as a partial helix; and
delivering cardiac pacing from the device to the heart by:
delivering a first cardiac pacing to the second chamber via the first electrode; and
delivering a second cardiac pacing to the first chamber via the second electrode.

12. The method of claim 11, wherein the wall tissue of the second chamber comprises a ventricular myocardium of the patient, wherein the wall tissue of the first chamber comprises an atrial endocardium of the patient, and wherein placing the second electrode in contact with the wall tissue of the first chamber comprises causing the second electrode to flexibly maintain contact with the atrial endocardium.

13. The method of claim 11, wherein a first pitch of the helix of the first electrode and a second pitch of the partial helix of the second electrode are substantially similar.

14. The method of claim 11, wherein the helix of the first electrode and the partial helix of the second electrode are wound in a same direction.

15. The method of claim 11, wherein the helix of the first electrode and the partial helix of the second electrode are wound in different directions.

16. The method of claim 11, wherein the elongated housing defines a longitudinal axis from a proximal end to the distal end, and wherein the second electrode is peripheral to the first electrode relative to the longitudinal axis.

17. The method of claim 11, wherein the second electrode extends from a first end to a second end, wherein the first electrode comprises one or more coatings configured to define a first electrically active region and the second electrode comprises one or more coatings configured to define a second electrically active region, and wherein the first electrically active region is more distal from the distal end of the elongated housing than the second electrically active region.

18. The method of claim 17, wherein the second end of the second electrode is a free floating end.

19. The method of claim 11, wherein the device further comprises at least one steroid eluting element configured to elute a steroid proximate to at least one of the first electrode or the second electrode.

20. The method of claim 11, wherein the first chamber comprises an atrium of the heart and wherein the second chamber comprises a ventricle of the heart.

* * * * *